(12) United States Patent
Berent et al.

(10) Patent No.: US 8,808,261 B2
(45) Date of Patent: Aug. 19, 2014

(54) URETERAL BYPASS DEVICES AND PROCEDURES

(76) Inventors: Allyson Cortney Berent, New York, NY (US); Charles Winston Weisse, New York, NY (US)

( * ) Notice: Subject to any disclaimer, the term of this patent is extended or adjusted under 35 U.S.C. 154(b) by 0 days.

(21) Appl. No.: 13/326,678

(22) Filed: Dec. 15, 2011

(65) Prior Publication Data

US 2012/0157833 A1      Jun. 21, 2012

Related U.S. Application Data

(60) Provisional application No. 61/423,285, filed on Dec. 15, 2010.

(51) Int. Cl.
*A61F 5/44* (2006.01)
*A61B 17/11* (2006.01)
*A61B 5/20* (2006.01)

(52) U.S. Cl.
CPC .. *A61B 17/11* (2013.01); *A61B 5/20* (2013.01)
USPC ........................................................ 604/332

(58) Field of Classification Search
USPC ........................................................ 604/544
See application file for complete search history.

(56) References Cited

U.S. PATENT DOCUMENTS

| | | | | |
|---|---|---|---|---|
| 3,875,941 | A * | 4/1975 | Adair | 604/540 |
| 4,057,066 | A * | 11/1977 | Taylor | 604/180 |
| 4,397,647 | A * | 8/1983 | Gordon | 604/180 |
| 4,610,657 | A | 9/1986 | Densow | |
| 4,692,149 | A * | 9/1987 | Rosenberg et al. | 604/99.02 |
| 4,790,809 | A * | 12/1988 | Kuntz | 604/8 |
| 4,957,479 | A | 9/1990 | Roemer | |
| 5,059,183 | A * | 10/1991 | Semrad | 604/158 |
| 5,224,953 | A * | 7/1993 | Morgentaler | 606/192 |

(Continued)

FOREIGN PATENT DOCUMENTS

EP          1051989        11/2000

OTHER PUBLICATIONS

Holger Gerullis, Thorsten H. Ecke, Klaus Schwartmann, Christoph J. Heuck, Christoph Elmer, Jens W. Bagner, Sunil Kocheril, and Thomas Otto; Nephrocutaneous Bypass in Ureteral Obstruction, Surgical Techniques in Urology; 2010, 480-485.

(Continued)

*Primary Examiner* — Susan Su
*Assistant Examiner* — Guy K Townsend
(74) *Attorney, Agent, or Firm* — Hartman Global IP Law; Gary M. Hartman; Domenica N. S. Hartman

(57) ABSTRACT

A ureteral bypass device and procedure suitable for performing internal urinary diversions within patients, including patients such as humans and veterinary animals (cats and dogs). The device includes a nephrostomy catheter having a proximal end, an oppositely-disposed distal end, and means for securing the distal end within the renal pelvis of a kidney of a patient, a cystostomy catheter having a proximal end, an oppositely-disposed distal end, and means for securing the distal end of the cystostomy catheter within the urinary bladder of the patient, and an adaptor fluidically connected to the proximal ends of the nephrostomy and cystostomy catheters so as to fluidically connect the nephrostomy and cystostomy catheters together through the adaptor. If implanted subcutaneously, the adaptor may include an entry site that has a self-sealing septum that can be accessed with a needle while the device remains implanted and secured under the skin to subcutaneous tissue.

31 Claims, 4 Drawing Sheets

(56) References Cited

U.S. PATENT DOCUMENTS

| | | | |
|---|---|---|---|
| 5,308,318 A * | 5/1994 | Plassche, Jr. | 604/540 |
| 5,401,257 A | 3/1995 | Chevalier et al. | |
| 5,792,095 A | 8/1998 | Kissinger | |
| 6,039,712 A | 3/2000 | Fogarty et al. | |
| 6,197,005 B1 | 3/2001 | Gerlach et al. | |
| 6,254,589 B1 | 7/2001 | Raoz | |
| 6,364,868 B1 * | 4/2002 | Ikeguchi | 604/514 |
| 6,656,146 B1 * | 12/2003 | Clayman et al. | 604/8 |
| 6,669,708 B1 * | 12/2003 | Nissenbaum et al. | 606/153 |
| 6,685,744 B2 | 2/2004 | Gellman et al. | |
| 6,699,216 B2 * | 3/2004 | Ikeguchi | 604/96.01 |
| 7,018,384 B2 | 3/2006 | Skakoon | |
| 7,037,345 B2 | 5/2006 | Bottcher et al. | |
| 7,044,981 B2 | 5/2006 | Liu et al. | |
| 7,316,663 B2 | 1/2008 | Whitmore, III | |
| 7,507,218 B2 | 3/2009 | Aliski et al. | |
| 7,513,892 B1 | 4/2009 | Haaralo et al. | |
| 7,722,677 B2 | 5/2010 | Ward | |
| 8,192,500 B2 | 6/2012 | Chung | |
| 2004/0153112 A1 * | 8/2004 | Nissenbaum et al. | 606/185 |
| 2006/0142732 A1 | 6/2006 | Karmarkar et al. | |
| 2006/0200079 A1 * | 9/2006 | Magnusson | 604/164.1 |
| 2007/0026043 A1 * | 2/2007 | Guan et al. | 424/426 |
| 2007/0049907 A1 * | 3/2007 | Fischer et al. | 604/544 |
| 2007/0060914 A1 * | 3/2007 | Magnusson | 604/544 |
| 2007/0100299 A1 | 5/2007 | Magnusson | |
| 2007/0299409 A1 * | 12/2007 | Whitbourne et al. | 604/264 |

OTHER PUBLICATIONS

Francois Desgrandchamps, Stephane Lerous, Vincent Ravery, Ghislain Bochereau, Philippe Menut, Paul Meria, Philippe Ballanger, and Pierre Teillac; Subcutaneous Pyelovesical Bypass as Replacement for Standard Percutaneous Nephrostomy for Palliative Urinary Diversion: Prospective Evaluation of Patient's Quality of Life; Journal of Endourology; vol. 21, No. 2, Feb. 2007.

A. Jurczok, H. Loertzer, S. Wager, P. Fornara; Subcutaneous Nephrovesical and Nephrocutaneous Bypass; Gynecologic and Obstetric Investigation; 2005; 59: 144-148.

David G. Bell, Marc Anthony Fischer; Palliative Subcutaneous Tunneled Nephrostomy Tube (PSTN): A simple and effective technique for management of malignant extrinsic ureteral obstruction; The Canadian Journal of Urology; Feb. 2002.

Michel E. Jabbour, Francois Desgrandchamps, Emil Angelescu, Pierre Teillac and Alain Le Duc; Percutaneous Implantation of Subcutaneous Prosthetic Ureters: Long-Term Outcome; Journal of Endourology; vol. 15, No. 6, Aug. 2001; 611-614.

Israel Nissenkorn nd Yehoshua Gdor; Nephrovesical Subcutaneous Stent: an Alternative to Permanent Nephrostomy; The Journal of Urology; vol. 163, 528-530, Feb. 2000.

S. Mjinhas, H.C. Irving, S.N. Lloyd, I. Eardley, A.J. Browning and A.D. Joyce; Extra-anatomic stents in ureteric obstruction: experience and complications; BJU International (1999), 84, 762-764.

Francois Desgrandchamps, Olivier Cussenot, Paul Meria, Ariane Cortesse, Pierre Teillac and Alain Le Duc; Subcutaneous Urinary Diversions for Palliative Treatment of Pelvic Malignancies; The Journal of Urology; vol. 154, 367-370, Aug. 1995.

Stephen Y. Nakada, Marshall E. Hicks, Adam J.Gerber, Daniel Picus, J. Stuart Wolf, and Ralph V. Clayman; Subcutaneous Urinary Diversion Utilizing a Nephrovesical Stent: A superior Alternative to Long-Term External Drainage; Urology, Mar. 1995, vol. 45, No. 3.

* cited by examiner

URETERAL BYPASS DEVICES AND PROCEDURES

CROSS REFERENCE TO RELATED APPLICATIONS

This application claims the benefit of U.S. Provisional Application No. 61/423,285, filed Dec. 15, 2010, the contents of which are incorporated herein by reference.

BACKGROUND OF THE INVENTION

The present invention generally relates to devices and procedures suitable for treating patients having ureteral obstructions or the like. More particularly, this invention relates to a ureteral bypass device and procedures for implanting the device, for example, by placing the device under the skin (subcutaneously) or within the abdominal cavity (intra-abdominally) of a patient. The device utilizes catheters and locking/retention mechanisms adapted to retain distal ends of the catheters within the renal pelvis and urinary bladder to avoid inadvertent dislodgement, as well as provide a seal to the kidney and bladder tissues to prevent urine leakage after device placement. The device further includes a port adapted to enable sampling, flushing, and testing the entire device for diagnostic or therapeutic purposes, without the need for invasive and expensive diagnostic methods.

Ureteral obstructions are a major surgical and endourological problem in both human and veterinary medicine. These obstructions can occur for various reasons, the most common of which include but are not limited to ureterolithiasis, urinary tract (intrinsic) or extrinsic neoplasia, and ureteral strictures. The traditional treatment in human medicine has involved the use of minimally invasive endourological procedures, for example, ureteral stenting, lithotripsy, ureteroscopic laser ablation, laparoscopic ureteral resection and anastomosis, and ureteropyelotomy. Minimally invasive treatments have nearly replaced open surgical procedures. In contrast, open surgical procedures such as ureterotomy, ureteral reimplantation and ureteronephrectomy are routinely performed for most causes of ureteral obstructions in companion animals (for example, canine and feline) due to the small nature of the canine (about 1 to 2 mm) and feline (about 0.3 to 0.4 mm) ureter and the minimal options available for interventional devices in animals of this size. Recently, the development of feline and canine double-pigtail ureteral stents has occurred and interventional treatments have become progressively more available. Unfortunately situations arise, particularly in small pediatric and veterinary patients, in whom ureteral decompression is necessary but traditional surgery or endourological procedures are associated with excessive morbidity or mortality, are impossible due to the size or anatomy, or are contraindicated.

In human medicine, if diversion procedures fail, implantation of an externalized percutaneous nephrostomy tube is usually necessary to provide either temporary or long-term drainage of the renal collection system. Placement of an externalized percutaneous nephrostomy tube is also possible in veterinary and pediatric patients for in-hospital stabilization, but is not feasible for long-term use. Major disadvantages associated with long-term use include the need for regular exchanges, the risk of urinary tract infections, urinary leakage and catheter dislodgement, social embarrassment, and an impaired quality of life reported for patients. Subcutaneous (or intra-abdominal) urinary diversion devices can internalize a nephrostomy catheter and allow the urine to drain to the urinary bladder through a subcutaneous tunnel. This eliminates most of the major disadvantages associated with externalized nephrostomy catheters because infection, regular nursing care, leakage, dislodgement, and an impaired quality of life are no longer prominent issues. Subcutaneous (or intra-abdominal) urinary diversion (bypass) devices become a more useful solution to very complicated medical problems associated with veterinary and pediatric patients, for whom externalized catheters are not a realistic option outside of a hospital setting.

A few variations on ureteral bypass devices have been reported in the past, varying from non-locking pigtail catheters, non-fenestrated double-pigtail stents, and non-locking double-lumen catheters with an inner silicone tube and an outer polyester sheath. For example, such devices have been reported or offered by Coloplast A/S. These various devices have been placed with surgical approaches requiring suturing of the tube to the bladder wall and renal capsule to prevent dislodgement and leakage. Short-term and long-term complications have been reported, with the major concerns being dislodgement, occlusion (encrustation), and difficulty in placement. However these devices still remain promising when all other traditional options have failed.

It is clear that there is an ongoing need for devices that are capable of treating various causes of ureteral obstruction, regardless of etiology, patient species, or size, in a rapid, simple, and safe manner. In particular, there is a need for a ureteral bypass device capable of overcoming the shortcomings of the prior art, particularly, dislodgement, discomfort, the currently invasive placement of the device, the large size of the device, as well as the concern for occlusion or encrustation of the device.

BRIEF DESCRIPTION OF THE INVENTION

The present invention provides a ureteral bypass device and procedure suitable for performing internalized urinary diversions within patients, including large patients such as human adults, as well as small patients such as children and animals.

According to a first aspect of the invention, the procedure includes creating an incision in the skin of a patient, implanting a nephrostomy catheter through the incision and securing a distal end of the nephrostomy catheter within the renal pelvis of a patient, implanting a cystostomy catheter through the incision and securing a distal end of the cystostomy catheter within the urinary bladder of the patient, fluidically connecting proximal ends of the nephrostomy and cystostomy catheters to a shunting port, and then subcutaneously implanting the shunting port to yield a subcutaneous ureteral bypass device, in which the nephrostomy and cystostomy catheters are fluidically connected together. The incision is then closed. The shunting port has a self-sealing septum that defines an entry site of the shunting port and is accessible through the skin of the patient to provide means for performing diagnostic and therapeutic procedures.

According to a second aspect of the invention, a ureteral bypass device includes a nephrostomy catheter having a proximal end, an oppositely-disposed distal end, and means for securing the distal end within the renal pelvis of a kidney of a patient, a cystostomy catheter having a proximal end, an oppositely-disposed distal end, and means for securing the distal end of the cystostomy catheter within the urinary bladder of the patient, and an adaptor fluidically connected to the proximal ends of the nephrostomy and cystostomy catheters so as to fluidically connect the nephrostomy and cystostomy catheters together through the port. The adaptor may be a shunting port that includes a self-sealing septum that provides an entry site for the port.

Another aspect of the invention is a procedure for performing an internal urinary diversion using a ureteral bypass device comprising the elements described above.

A technical effect of the invention is that the device is capable of use in the treatment of many, if not all, causes of ureteral obstruction, regardless of etiology, patient size or species. If the device includes a shunting port with an entry site, the entry site is preferably configured to provide access to the port that allows for testing, sampling and flushing of the device, and therefore enables occlusions, encrustation, and the like to be cleared or avoided without necessitating the removal of the device from the patient or the need for future surgical manipulation. The device is well suited for remaining indwelling long-term within a patient, preferably for periods of at least 36 months. In young children with anatomical anomalies, this allows the time for the urinary system to grow prior to the consideration of more dramatic reconstructive surgeries that would ideally be done at an older age.

Other aspects and advantages of this invention will be better appreciated from the following detailed description.

DETAILED DESCRIPTION OF THE INVENTION

The following describes what will be referred to as a ureteral bypass device (UBD) that is capable of treating causes of ureteral obstruction. The device can be used in humans (children and adults) and animals, regardless of etiology, species, or patient size, and can be optimized for the patient. In addition, the UBD of this invention beneficially allows for secure and facile placement of the device within the patient, as will be evident from the following discussion.

Figure 1:
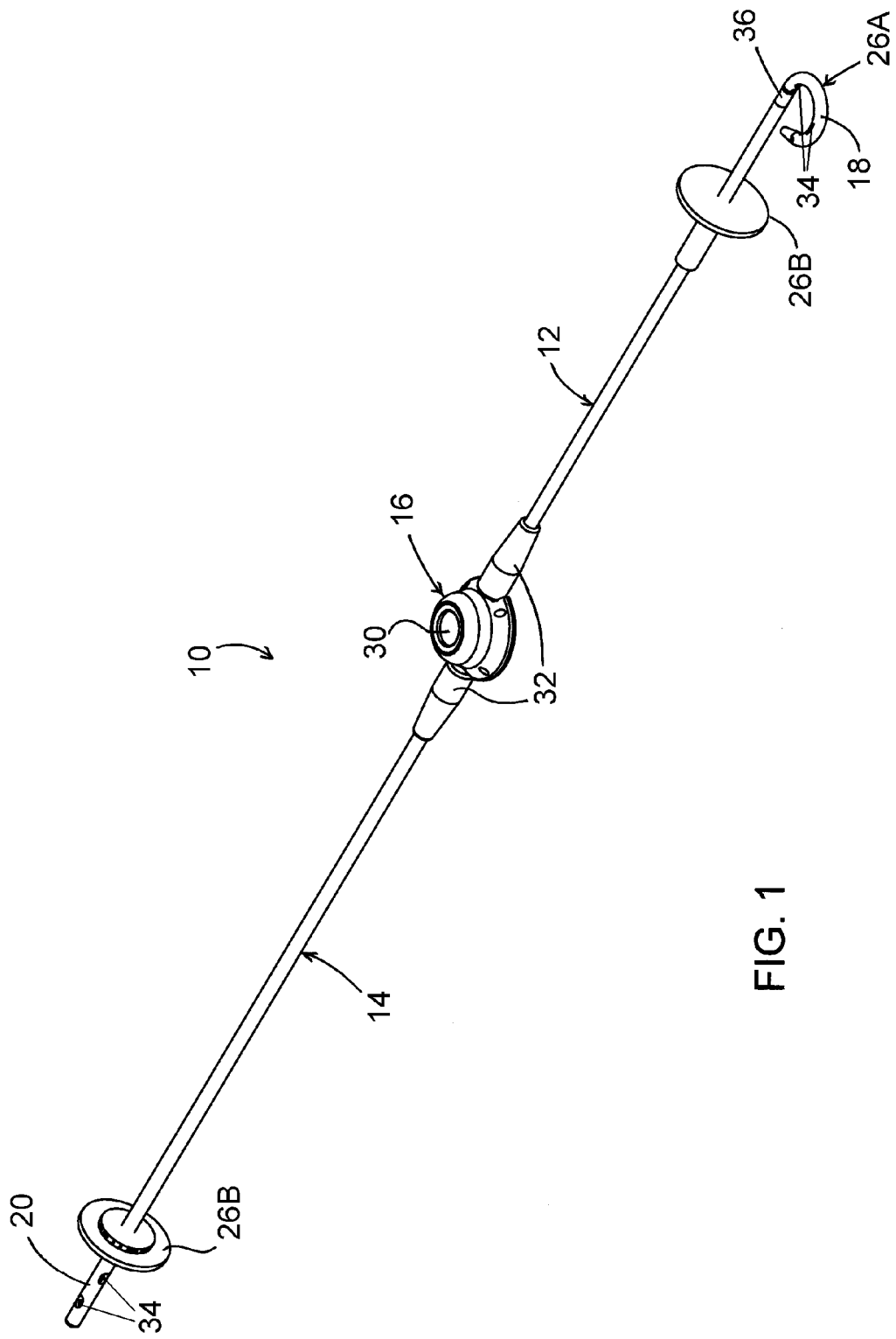
FIG. 1 is a perspective view of a ureteral bypass device in accordance with an embodiment of this invention.
Figure 2:
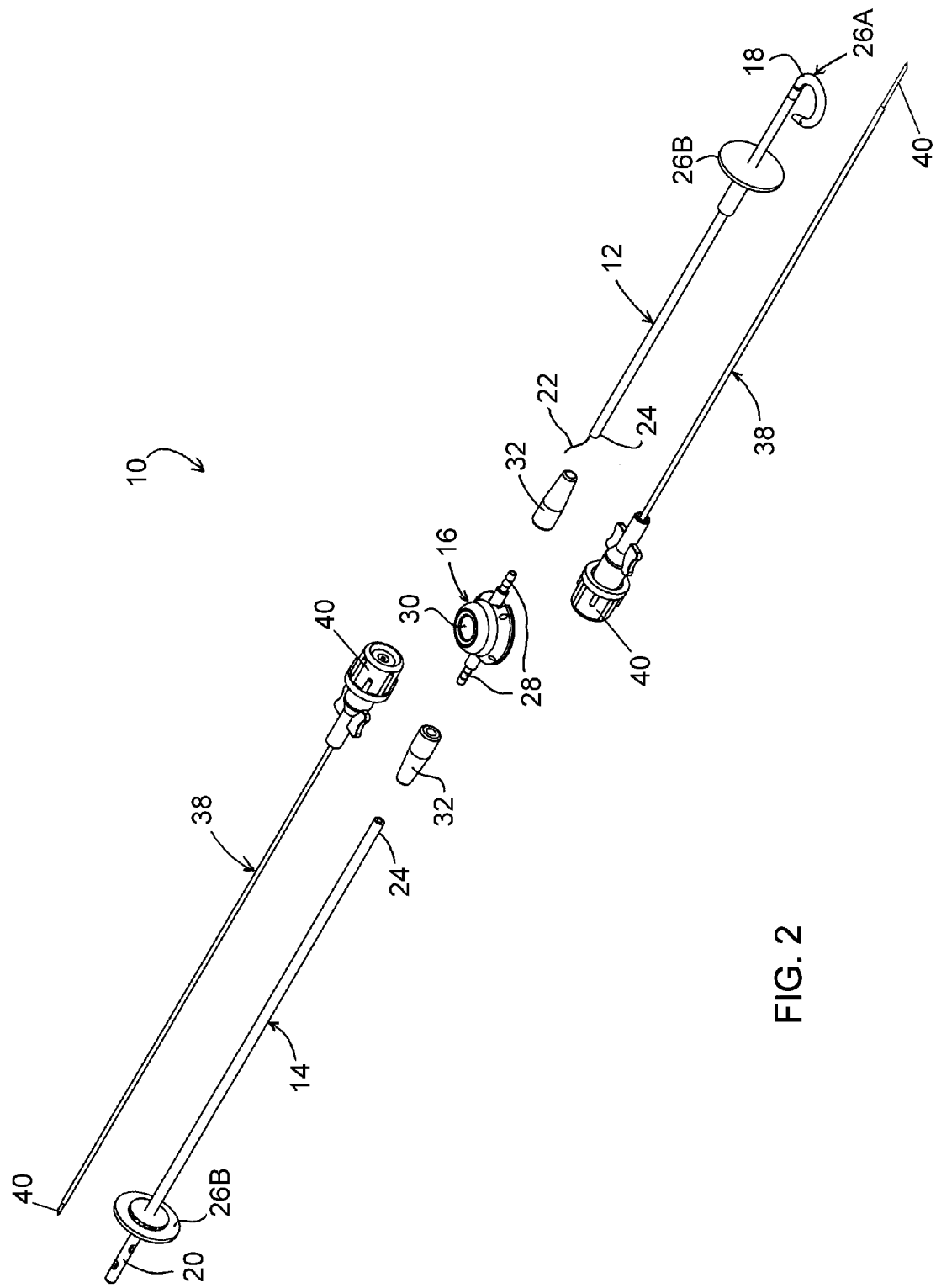
FIG. 2 is a perspective view of components of the ureteral bypass device of FIG. 1.

FIG. 1 represents a particular embodiment of a UBD 10 as comprising a pair of catheters 12 and 14 and a shunting adaptor 16 to which the catheters 12 and 14 are coupled. The adaptor 16 is represented in FIGS. 1 and 2 as being configured as a shunting port, though from the following discussion it will become apparent that the certain features of a port would not be necessary in all embodiments of the invention. Distal ends 18 and 20 of the catheters 12 and 14 are adapted to be placed within, respectively, the renal pelvis and urinary bladder of a patient. As such, the catheters 12 and 14 can be referred to as nephrostomy and cystostomy catheters, respectively, though it should be evident that the catheters 12 and 14 are configured differently from prior art catheters of types used in ureteral bypass procedures. Suitable sizes for the catheters 12 and 14 will depend on the size of the patient and the drainage requirements. The diameters of the catheters 12 and 14 are preferably larger than traditional ureteral stents (limited by natural ureteral size) to provide better drainage. As nonlimiting examples, catheter sizes of 5 to 6 Fr will typically be suitable for cats, 6 Fr will typically be suitable for dogs, 5 to 8 Fr will typically be suitable for children and adults, though larger sizes (for example, 5 to 30 Fr) are possible and could be used if necessary. The lengths of the catheters 12 and 14 can also be tailored to meet the particular requirements of a patient.

Each catheter 12 and 14 is preferably equipped with a locking mechanism that retains its respective distal end 18 and 20 within the renal pelvis or urinary bladder of the patient, respectively. As represented in FIG. 1, the distal end 18 of the nephrostomy catheter 12 is configured as a locking loop (pigtail) 26A capable of retaining the distal end 18 within the renal pelvis of a kidney for nephrostomy placement. To keep the locking loop 26A coiled after being placed inside the renal pelvis, a string (22 in FIG. 2) can be passed inside the catheter 12 from its locking distal end 18 and through a proximal end 24 of the catheter 12 at which the catheter 12 will be connected to the adaptor 16 (FIG. 1). For example, the catheter 12 may be fluidically connected to the adaptor 16 via a male fitting 28 of the adaptor 16, to which the catheter 12 is secured with a boot 32 formed of a biocompatible material, for example, silicone. The locking configuration shown for the distal end 18 in FIG. 1 can be maintained by entrapping the string 22 by and between the boot 32, the proximal end 24 of the catheter 12, and/or the fitting 28 (represented in FIG. 2 as a graduated barb). The distal end 20 of the bladder (cystostomy) catheter 14 can also be configured as a locking loop (pigtail) similar to the catheter 12 and its distal end 18. In FIG. 1, the distal end 20 of the catheter 14 is represented as straight and equipped with a cuff 26B adapted for adherence to the external serosal surface of a bladder. A particular example is a silicone catheter with a DACRON® cuff (or any other adhered material) 26B for organ pexy to prevent leakage and ensure stability. As represented in FIGS. 1 and 2, the nephrostomy catheter 12 can also be equipped with a cuff 26B, wherein the cuff 26B can be provided instead of, or in addition to, the locking loop 26A. The addition of a cuff 26B to each catheter 12 and 14 can be advantageous, in that the cuff 26B is able to form a secure adhesion without the need for direct attachment to the body wall for the kidney or urinary bladder (nephropexy or cystopexy), and in this manner promotes the ability of the catheters 12 and 14 to remain secure to the kidney capsule and bladder wall (serosa) and prevent leakage of urine during healing. The distal ends 18 and 20 of the catheters 12 and 14 are further represented as multifenestrated, in other words, having multiple fenestrations 34. As is visible for the catheter 12 in FIGS. 1 and 2, a radioopaque marker band 36 can be placed behind the last (most proximal) fenestration 34 to allow for fluoroscopic assurance that the entire loop 26A and all fenestrations 34 are within the renal pelvis to prevent any extravasation or leakage of urine.

FIGS. 1 and 2 represent the catheters 12 and 14 and the adaptor 16 as separate components that must be assembled, though it is also within the scope of the invention that the UBD 10 could be manufactured as a single unitary component. In either case, the catheters 12 and 14 and adaptor 16 are adapted to be entirely implanted within a patient, in other words, under the skin (subcutaneously) or within the abdominal cavity (intra-abdominally) of a patient. As represented in FIGS. 1 and 2, each catheter 12 and 14 can be coupled to the adaptor 16 with one of the catheter boots 32. In the embodiment of FIGS. 1 and 2, the boots 32 serve to prevent leaks, cover the locking string(s) 22, and secure the catheters 12 and 14 to the fittings 28 of the adaptor 16. The adaptor 16 can be configured to define an internal reservoir compartment (shunting port) that serves as a shunt between the catheters 12 and 14. The fittings 28 of the adaptor 16 are represented in FIG. 2 as male barbed fittings configured to provide male-to-male couplings with the catheters 12 and 14, and are therefore preferably sized to correspond to the size of the catheters 12 and 14 and drainage requirements of the UBD 10. In the embodiment of FIGS. 1 and 2, the adaptor 16 is equipped with two fittings 28, one for each of the catheters 12 and 14, so that the cystostomy catheter 14 fluidically communicates with a single nephrostomy catheter 12 through the compartment within the adaptor 16. However, the adaptor 16 can be equipped with additional fittings, for example, a third fitting that enables a second nephrostomy catheter 12 to be coupled to the adaptor 16, such that the UBD 10 can be implanted in the renal pelvis of each kidney of the patient and the cystostomy catheter 14 fluidically communicates with both nephrostomy catheters 12 (in the event of a bilateral ureteral obstruction). Advantageously, such a three-way design for the adaptor 16 eliminates the requirement in prior bilateral ureteral bypass procedures to implant two separate cystostomy catheters when necessary.

The adaptor 16 is also represented in FIGS. 1 and 2 as being equipped with an entry site 30, which is configured to provide an access to the adaptor 16 that allows for testing, sampling and flushing of the UBD 10, and therefore enables occlusions, encrustation, and the like to be cleared or avoided. If the UBD 10 is to be placed intra-abdominally, the adaptor 16 would not be required to have an entry site 30, in which case the adaptor 16 could essentially comprise two or more fittings 28 for connecting two or more nephrostomy catheters 12 to the cystostomy catheter 14. An advantage of the entry site 30 is that it allows for the UBD 10 to be tested using contrast material and fluoroscopic guidance to ensure the patency of the system, as well as for urine sampling of the system directly, in a sterile manner. The entry site 30 is preferably configured as a septum that can be punctured by a needle, for example, a Huber point non-coring needle, which enables for multiple sampling and needle access without leakage. The adaptor 16 can be placed so that its entry site 30, and particularly its septum, is in proximity to the patient's skin. As with ports employed with implantable venous access systems, the septum can be made of a self-sealing silicone rubber that can be punctured numerous and preferably thousands of times. Through its entry site 30, the UBD 10 can be tested, such as with a contrast material and fluoroscopy to ensure patency and no leakage, sampled for infection, urinalysis, etc., and flushed if an occlusion is determined to exist within the catheters 12 and 14 or the adaptor 16. If encrustation or occlusion has occurred, a needle can be used to inject a contrast material into the adaptor 16 via placing the needle through the patient's skin, through the entry site 30 of the adaptor 16, and into the portal of the adaptor 16 to enable documentation of the occlusion site, all while the patent is awake. The entire UBD 10 can then be flushed of debris through the entry site 30 of the adaptor 16 to remove the occlusion. Access to the UBD 10 through the entry site 30 is able to promote the safety and effectiveness of long-term management of the UBD 10 without necessitating the need for testing using an invasive procedure, such as renal puncture. Furthermore, the ability to flush the entire UBD 10 of debris to remove an occlusion is not only diagnostically beneficial, but can also be potentially therapeutic for the patient. Also, since access to both the kidney and bladder catheters 12 and 14 is possible under the skin, in the event either catheter 12 and 14 needs to be exchanged, the procedure can be performed through a small skin incision at the port site and performed over a guidewire using fluoroscopic visualization without the need for further surgery.

A preferred procedure for placing the UBD 10 within a patient is to use a modified version of the well-known modified-Seldinger technique utilizing a guidewire and preferably under fluoroscopic guidance. Alternatively, a direct-stick method can be performed without guidewire access. Using a modified-Seldinger technique, an incision is made at a sterilized site through which the components of the UBD 10 will be implanted. It is not necessary to implant the completed assembly for the UBD 10 shown in FIG. 1, but instead, the catheters 12 and 14 and adaptor 16 can be implanted separately (if not manufactured as a unitary component). Punctures can be made in each of the renal pelvis and the urinary bladder with separate renal access needles (not shown), suitably sized for the desired guidewire size (typically 18 gauge renal access needle with a 0.035" guidewire), For both nephrostomy and cystostomy placement, a guidewire can then be advanced through the access needle and coiled inside the renal pelvis or urinary bladder. The access needle is then removed over the wire and the distal ends 18 and 20 of the catheters 12 and 14 can be respectively placed over the wire, inside the renal pelvis and urinary bladder. Each catheter 12 and 14 is preloaded with a hollow trocar 38 to maintain the stiffness and pushability to advance the respective catheter 12/14 over the wire. Whether the patient is human or animal, if the distal end 18 of the nephrostomy catheter 12 is configured as a locking loop 26A, the renal pelvis is preferably dilated to accommodate the locking loop 26A. An alternative is to use the hollow trocar 38 with a sharp stylette 40 (the sharp tip and cap of which are seen in FIG. 2) to directly puncture the renal pelvis or urinary bladder without the use of the modified-Seldinger technique or need for a guidewire.

The distal end 18 of the nephrostomy catheter 12 can then be actuated with the string 22 to form the locking loop 26A, which prevents the catheter 12 from becoming dislodged once placed within the patient. Similarly, the distal end 20 of the cystostomy catheter 14 is secured with the cuff 26B (or, if so equipped, a locking loop 26A) to prevent the catheter 14 from becoming dislodged from the urinary bladder. Both catheters 12 and 14 can be cut to an appropriate length, based on patient needs, prior to being fluidically connected to the adaptor 16 via the fittings 28. The boots 32 can then be advanced onto the proximal ends 24 of the catheters 12 and 14 to connect and secure the catheters to the adaptor 16. The locking string(s) 22 of the catheter(s) 12 and/or 14 are secured to the adaptor 16 by advancing the boots 32 over the junctions formed by the fittings 28 and the catheters 12 and 14. The adaptor 16 is then implanted and secured under the skin to subcutaneous tissue, after which the incision can be closed. As previously noted, the incision is preferably closed so that the entry site 30 of the adaptor 16 (if so equipped) is accessible through the patient's skin with simple needle access. The completed assembly of the UBD 10 is entirely located internally of the patient, and typically located subcutaneously, on the surface of the abdominal wall, though a completely intra-abdominal option is also possible. The entry site 30 is accessible through the patient's skin to provide a leak-free access port for testing, sampling and flushing of the UBD 10 with an appropriate needle, such as a non-coring Huber needle.

From the above, it should be appreciated that the present invention provides for facile and secure implantation of the UBD 10 within a patient. The UBD 10 provides the capability for easy sampling of the UBD 10 for infection, urinalysis, or the like, allows for testing the entire UBD 10 with contrast material to ensure patency and no leakage. The UBD 10 can also be flushed if an occlusion is discovered within the UBD 10, or serially to prevent an occlusion. Needle access directly into this UBD 10 (via the entry site 30) makes long-term management of the UBD 10 safe, non-painful, non-invasive, and effective without the requirement for risky, invasive testing procedures that provide only diagnostic utility without any therapeutic options.

In addition, if the UBD 10 is assembled from individual components (catheters 12 and 14 and adaptor 16), replacement of one of the catheters 12 or 14 or adaptor 16 can be accomplished without requiring complete removal of the entire UBD 10 or an additional invasive surgery. The catheters 12 and 14 and adaptor 16 can be segmentally exchanged over a guidewire if necessary, which can be readily accomplished using fluoroscopic guidance and a guidewire without complete removal and exchange of the entire UBD 10. As a result, replacement of components of the UBD 10 can be accomplished through a small incision in the patient's skin covering the entry site 30 of the adaptor 16, without requiring entry into the abdomen. This capability circumvents the need for a major surgical procedure to replace the UBD 10 in its entirety, and allows utilization of the same tunnel that was formed previously within the patient. A UBD 10 assembled from individual components also enables physicians and veterinarians to choose if he/she prefers to use catheters 12 and 14 with two locking-loops 26A or, as represented in FIGS. 1 and 2, a single locking loop 26A and a straight catheter 14 for individual patients (perhaps depending upon on completely percutaneous placement versus open surgical placement).

Finally, in patients that require bilateral diversion (about 10 to 20%, depending on cause), the adaptor 16 can have a three-way configuration, by which the adaptor 16 is equipped with a third fitting 28 to allow a second nephrostomy catheter to be connected to the single cystostomy catheter 14 through the adaptor 16. As a result, only a single access point is required to the urinary bladder, and less artificial material is implanted in the patient.

A UBD 10 of the type shown in FIGS. 1 and 2 has been trialed in thirty-four feline patients and two canine patients for various causes of ureteral obstruction. The trials showed the UBD 10 to be successful and patent for urinary drainage long-term (typically at least 24 months and in some cases more than three years), with very few associated complications. None of the devices developed encrustation, occlusion or dislodgement in the long-term with the practice of serial flushing (every 3-6 months when necessary on an out-patient basis).

Figure 3:
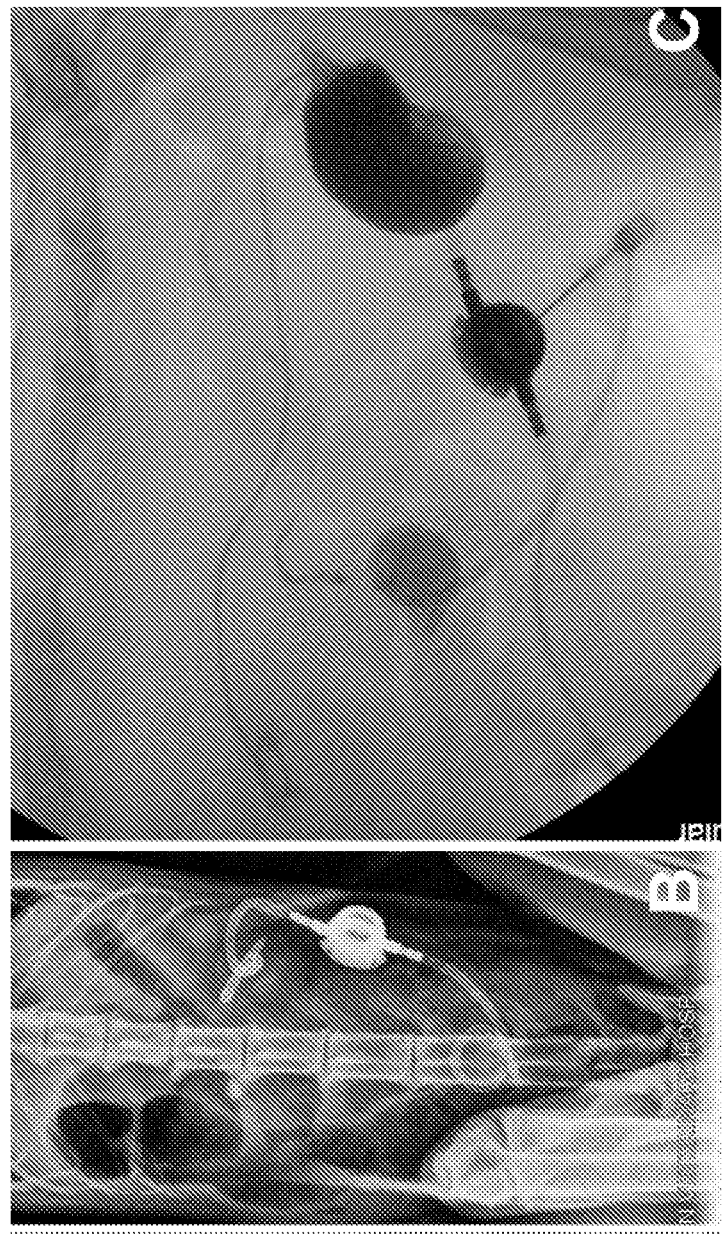
FIGS. 3 and 4 are images showing ureteral bypass devices of the type shown in FIG. 1, implanted in feline patients.

FIG. 3 shows two images of feline patients in which UBDs of this invention have been implanted. In the lefthand surgical image (B), a ventrodorsal radiograph shows a UBD implanted on the left side of a feline patient. The proximal ends of each of the nephrostomy and cystostomy catheters are shown attached to a metallic adaptor (shunting port) and their distal ends are equipped with a locking loop coiled within, respectively, the renal pelvis or urinary bladder of the patient. Image (C) is a lateral fluoroscopic image of a feline patient during injection of a contrast material into the port of a UBD through its entry site using a non-coring Huber needle. The Huber needle has been inserted through a silicone rubber septum that forms the entry site under the skin, and the UBD is being flushed with the contrast material under fluoroscopic guidance. The contrast material can be seen as filling the renal pelvis, urinary bladder and ipsilateral ureter, confirming patency of the device. This particular patient also has a double-pigtail ureteral stent inside the contralateral ureter that had been placed previously.

Figure 4:
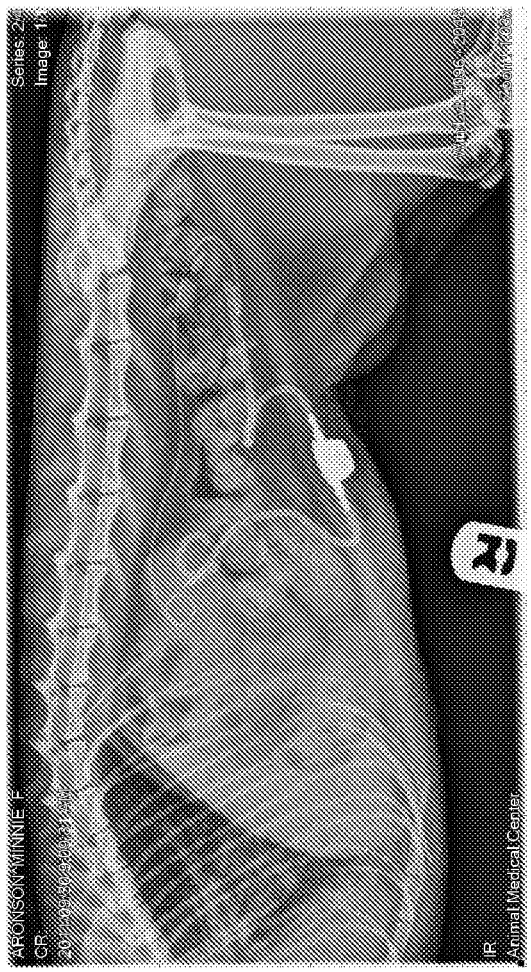

FIG. 4 shows another image of a feline patient in which a UBD of this invention has been implanted. The image in FIG. 4 is a lateral abdominal radiograph of the patient with a left-sided ureteral stent and a right-sided UBD of this invention. The nephrostomy catheter of the UBD has a locking loop within the renal pelvis and a DACRON®/silicone cuff attached to the renal capsule. The nephrostomy catheter is tunneled through the body wall of the renal pelvis to the port, which is located in the subcutaneous tissue. The cystostomy catheter is a straight, multi-fenestrated catheter that passes through the apex of the urinary bladder and is equipped with a DACRON®/silicone cuff adhered to the outside of the bladder wall (serosa) for security. In contrast to the UBDs of FIG. 3, the UBD in FIG. 4 is not pexied to any internal body wall but instead to the rention cuffs.

While the invention has been described in terms of preferred embodiments, it is apparent that other forms could be adopted by one skilled in the art. For example, the ureteral bypass device could differ in appearance and construction from the embodiment disclosed, the functions of each component of the device could be performed by components of different construction but capable of a similar (though not necessarily equivalent) function, and appropriate materials could be substituted for those noted. Therefore, the scope of the invention is to be limited only by the following claims.

The invention claimed is:

1. A procedure for performing an internal urinary diversion that bypasses a ureter of a patient between a kidney and urinary bladder of the patient, the procedure comprising:
creating an incision in the skin of a patient;
implanting a nephrostomy catheter through the incision so that the nephrostomy catheter is entirely external of the ureter, and securing a first end of the nephrostomy catheter within the renal pelvis of a kidney of the patient;
implanting a cystostomy catheter through the incision so that the cystostomy catheter is entirely external of the ureter, and securing a first end of the cystostomy catheter within the urinary bladder of the patient;
removably assembling second ends of the nephrostomy and cystostomy catheters to an adaptor with connectors to yield a ureteral bypass device in which the nephrostomy and cystostomy catheters are fluidically connected together through the adaptor and the ureteral bypass device defines an internalized urinary diversion through which urinary drainage occurs from the kidney to the urinary bladder and entirely bypasses the ureter of the patient, the connectors enabling interchangeability of the nephrostomy and cystostomy catheters with additional nephrostomy and cystostomy catheters, the adaptor having an internal reservoir compartment and an entry site that comprises a self-sealing septum; and
implanting the adaptor and closing the incision so that the ureteral bypass device is entirely located internally of the patient, the entry site of the adaptor is subcutaneously located in proximity to skin of the patient, and the septum is accessible through the skin of the patient to enable performing diagnostic and therapeutic procedures including testing, sampling and flushing of the ureteral bypass device in its entirety while the ureteral bypass device is within the patient and without necessitating removal of the ureteral bypass device from the patient or surgical manipulation.

2. The procedure according to claim 1, wherein the first end of the nephrostomy catheter is secured within the renal pelvis as a result of the first end being configured as a locking loop.

3. The procedure according to claim 1, wherein the first end of the cystostomy catheter is secured within the urinary bladder as a result of the first end being configured as a locking loop.

4. The procedure according to claim 1, wherein the first end of the nephrostomy catheter is secured within the renal pelvis with a cuff that is pexied to an external surface of the kidney with or without a locking loop.

5. The procedure according to claim 1, wherein the first end of the cystostomy catheter is secured within the urinary bladder with a cuff that is pexied to an external surface of the urinary bladder with or without a locking loop.

6. The procedure according to claim 1, further comprising:
inserting a needle through the skin of the patient and through the entry site; and then
performing at least one step chosen from the group consisting of testing, sampling and flushing the ureteral bypass device.

7. The procedure according to claim 6, wherein the step comprises sampling fluid within the ureteral bypass device for infection and urinalysis while the ureteral bypass device remains implanted within the patient.

8. The procedure according to claim 6, wherein the step comprises testing the ureteral bypass device while the ureteral bypass device remains implanted within the patient by injecting a contrast material into the ureteral bypass device so that the contrast material subsequently flows into the kidney and the urinary bladder to ensure patency and prevent occlusion.

9. The procedure according to claim 6, wherein the step comprises:
determining whether an occlusion is present in the ureteral bypass device; and then
flushing the occlusion from the ureteral bypass device while the ureteral bypass device remains implanted within the patient.

10. The procedure according to claim 1, further comprising:
implanting a second nephrostomy catheter through the incision and securing a first end of the second nephrostomy catheter within the renal pelvis of a second kidney of the patient; and then
fluidically connecting the second nephrostomy catheter to the adaptor so as to fluidically connect the second nephrostomy catheter to the cystostomy catheter.

11. The procedure according to claim 1, wherein the patient is an animal.

12. The procedure according to claim 11, wherein each of the nephrostomy and cystostomy catheters has a diameter within a range of about 5 to about 30 Fr.

13. The procedure according to claim 1, wherein the patient is a child or adult human.

14. The procedure according to claim 13, wherein each of the nephrostomy and cystostomy catheters has a diameter within a range of about 5 to about 8 Fr.

15. The procedure according to claim 1, wherein the ureteral bypass device remains indwelling long-term within the patient.

16. The procedure according to claim 1, further comprising:
creating a second incision in the skin of the patient;
disconnecting the adaptor from at least one of the nephrostomy and cystostomy catheters; and then
removing one or more of the adaptor and the nephrostomy and cystostomy catheters but not the ureteral bypass device in its entirety.

17. A ureteral bypass device adapted to provide an internal urinary diversion that bypasses a ureter of a patient between a kidney and urinary bladder of the patient, the ureteral bypass device comprising:
a nephrostomy catheter having oppositely-disposed first and second ends, means for adhering the nephrostomy catheter to an external surface of the kidney, and means for securing the first end within the renal pelvis of a kidney of a patient;
a cystostomy catheter having oppositely-disposed first and second ends, means for adhering the cystostomy catheter to an external surface of the urinary bladder, and means for securing the first end of the cystostomy catheter within the urinary bladder of the patient; and
an adaptor removably assembled with connectors to the second ends of the nephrostomy and cystostomy catheters so as to fluidically connect the nephrostomy and cystostomy catheters together through the adaptor and thereby form the ureteral bypass device that defines an internalized urinary diversion through which urinary drainage occurs from the kidney to the urinary bladder and bypasses the ureter of the patient, the connectors enabling interchangeability of the nephrostomy and cystostomy catheters with additional nephrostomy and cystostomy catheters, the adaptor having an internal reservoir compartment and an entry site that comprises a self-sealing septum, the adaptor being configured to subcutaneously locate the entry site in proximity to skin of a patient after implantation of the ureteral bypass device in the patient and to provide access to the entry site through the skin to enable performing diagnostic and therapeutic procedures including testing, sampling and flushing of the ureteral bypass device in its entirety while the ureteral bypass device is within the patient and without necessitating removal of the ureteral bypass device from the patient or surgical manipulation.

18. The ureteral bypass device according to claim 17, wherein the securing means of the nephrostomy and cystostomy catheters are chosen from the group consisting of multi-fenestrated locking loops and cuffs adapted to be organ pexied.

19. The ureteral bypass device according to claim 17, wherein the first end of at least one of the nephrostomy and cystostomy catheters is straight and multi-fenestrated.

20. The ureteral bypass device according to claim 17, wherein each of the nephrostomy and cystostomy catheters has a diameter within a range of about 5 to about 30 Fr.

21. The ureteral bypass device according to claim 17, wherein each of the nephrostomy and cystostomy catheters has a diameter within a range of about 5 to about 8 Fr.

22. The ureteral bypass device according to claim 17, wherein each of the nephrostomy and cystostomy catheters has a diameter within a range of about 5 to about 6 Fr.

23. The ureteral bypass device according to claim 17, further comprising a second nephrostomy catheter having oppositely-disposed first and second ends, and means for securing the first end of the second nephrostomy catheter within the renal pelvis of a second kidney of a patient, the adaptor being fluidically connected to the second end of the second nephrostomy catheter so as to fluidically connect the second nephrostomy catheter to the cystostomy catheter through the adaptor.

24. A procedure for performing an intra-abdominal urinary diversion with an implanted ureteral bypass device that bypasses a ureter of a patient between a kidney and urinary bladder of the patient, the procedure comprising:
creating an incision in the skin of a patient;
implanting a nephrostomy catheter through the incision so that the nephrostomy catheter is entirely external of the ureter, and securing a first end thereof within the renal pelvis of a kidney of the patient;

implanting a cystostomy catheter through the incision so that the cystostomy catheter is entirely external of the ureter, and securing a first end thereof within the urinary bladder of the patient;

removably assembling second ends of the nephrostomy and cystostomy catheters to an adaptor with connectors to fluidically connect the nephrostomy and cystostomy catheters together and thereby form a ureteral bypass device that defines an internalized urinary diversion through which urinary drainage occurs from the kidney to the urinary bladder and entirely bypasses the ureter of the patient, the connectors enabling interchangeability of the nephrostomy and cystostomy catheters with additional nephrostomy and cystostomy catheters, the adaptor having an internal reservoir compartment and an entry site that comprises a self-sealing septum; and implanting the adaptor and closing the incision so that the ureteral bypass device is entirely located internally of the patient, the entry site of the adaptor being subcutaneously located in proximity to skin of the patient to provide access to the entry site through the skin to enable performing diagnostic and therapeutic procedures including testing, sampling and flushing of the ureteral bypass device in its entirety while the ureteral bypass device is within the patient and without necessitating removal of the ureteral bypass device from the patient or surgical manipulation.

25. The procedure according to claim 24, further comprising:
   inserting a needle through the skin of the patient and through an entry site of the adaptor; and then
   performing at least one step chosen from the group consisting of testing, sampling and flushing the ureteral bypass device.

26. The procedure according to claim 25, wherein the step comprises sampling fluid within the ureteral bypass device for infection and urinalysis while the ureteral bypass device remains implanted within the patient.

27. The procedure according to claim 25, wherein the step comprises testing the ureteral bypass device while the ureteral bypass device remains implanted within the patient by injecting a contrast material into the ureteral bypass device so that the contrast material subsequently flows into the kidney and the urinary bladder.

28. The procedure according to claim 25, wherein the step further comprises:
   determining whether an occlusion is present in the ureteral bypass device; and then
   flushing the occlusion from the ureteral bypass device while the ureteral bypass device remains implanted within the patient.

29. The procedure according to claim 24, further comprising:
   implanting a second nephrostomy catheter through the incision and securing a first end of the second nephrostomy catheter within the renal pelvis of a second kidney of the patient; and then
   fluidically connecting the second nephrostomy catheter to the adaptor so as to fluidically connect the second nephrostomy catheter to the cystostomy catheter.

30. The procedure according to claim 24, wherein the ureteral bypass device remains indwelling long-term within the patient.

31. The procedure according to claim 24, further comprising:
   creating a second incision in the skin of the patient;
   disconnecting the adaptor from at least one of the nephrostomy and cystostomy catheters; and then
   removing one or more of the adaptor and the nephrostomy and cystostomy catheters but not the ureteral bypass device in its entirety.

* * * * *